United States Patent
Kim et al.

(10) Patent No.: US 10,622,092 B2
(45) Date of Patent: *Apr. 14, 2020

(54) METHOD AND SYSTEM FOR FACILITATING PHYSIOLOGICAL COMPUTATIONS

(71) Applicant: HeartFlow, Inc., Redwood City, CA (US)

(72) Inventors: Jin Kim, Daly City, CA (US); Michael Singer, Belmont, CA (US)

(73) Assignee: HeartFlow, Inc., Redwood City, CA (US)

( * ) Notice: Subject to any disclaimer, the term of this patent is extended or adjusted under 35 U.S.C. 154(b) by 261 days.

This patent is subject to a terminal disclaimer.

(21) Appl. No.: 14/988,040

(22) Filed: Jan. 5, 2016

(65) Prior Publication Data

US 2016/0132657 A1  May 12, 2016

Related U.S. Application Data

(63) Continuation of application No. 13/625,628, filed on Sep. 24, 2012, now Pat. No. 9,262,581.

(51) Int. Cl.
   *G06G 7/48* (2006.01)
   *G16B 5/00* (2019.01)
   *G16H 50/50* (2018.01)

(52) U.S. Cl.
   CPC ............... *G16B 5/00* (2019.02); *G16H 50/50* (2018.01)

(58) Field of Classification Search
   None
   See application file for complete search history.

(56) References Cited

U.S. PATENT DOCUMENTS

| | | | | | |
|---|---|---|---|---|---|
| 5,687,737 A | * | 11/1997 | Branham | ............ | A61B 5/0422 600/509 |
| 5,729,670 A | * | 3/1998 | Strumolo | ................ | G06T 17/20 345/420 |
| 5,740,802 A | * | 4/1998 | Nafis | ................... | G06F 19/3406 348/E13.014 |

(Continued)

OTHER PUBLICATIONS

Khokhlov, Alexei M. "Fully threaded tree algorithms for adaptive refinement fluid dynamics simulations." Journal of Computational Physics 143.2 (1998): 519-543.*

(Continued)

*Primary Examiner* — Rehana Perveen
*Assistant Examiner* — Nithya J. Moll
(74) *Attorney, Agent, or Firm* — Bookoff McAndrews, PLLC

(57) ABSTRACT

A system for noninvasively determining at least one physiological characteristic of a patient may include at least one computer system configured to, using a three-dimensional surface mesh model created using patient-specific imaging data, create a three-dimensional combined surface and volume mesh model, including at least a first model portion that has a different spatial resolution than at least a second model portion. The computer system may be further configured to input the three-dimensional surface and volume mesh model into a fluid simulation system and determine a measurement of the physiological characteristic, using the fluid simulation system.

19 Claims, 12 Drawing Sheets

(56) References Cited

U.S. PATENT DOCUMENTS

| | | | |
|---|---|---|---|
| 6,169,917 B1* | 1/2001 | Masotti | A61B 6/4441 600/407 |
| 2004/0153128 A1 | 8/2004 | Suresh et al. | |
| 2010/0130878 A1 | 5/2010 | Lasso et al. | |
| 2010/0280352 A1* | 11/2010 | Ionasec | A61B 5/0263 600/407 |
| 2010/0298719 A1* | 11/2010 | Kock | A61B 5/02028 600/485 |
| 2012/0041318 A1 | 2/2012 | Taylor | |
| 2012/0041739 A1 | 2/2012 | Taylor | |
| 2012/0053918 A1 | 3/2012 | Taylor | |

OTHER PUBLICATIONS

International Search Report and Written Opinion dated Jul. 3, 2014, in corresponding International Application No. PCT/US2013/061235, filed on Sep. 23, 2013 (10 pages).

International Preliminary Report on Patentability and Written Opinion dated Apr. 2, 2015, in corresponding International Application No. PCT/US2013/061235, filed on Sep. 23, 2013 (9 pages).

"Patient-Specific Modeling of Cardiovascular Mechanics", Taylor and Figueroa. Copyright 2009.

"Image-Based Modeling of Blood Flow and Vessel Wall Dynamics Applications, Methods and Future Directions", Taylor and Steinman. Sixth International Bio-Fluid Mechanics Symposium and Workshop, Mar. 28-30, 2008, Pasadena, California.

"Measurement of Fractional Flow Reserve to Assess the Functional Severity of Cornary-Artery Stenosis", Pijls et al. Copyright © 1996 Massachusetts Medical Society.

* cited by examiner

METHOD AND SYSTEM FOR FACILITATING PHYSIOLOGICAL COMPUTATIONS

CROSS-REFERENCE TO RELATED APPLICATIONS

This application is a continuation of U.S. Nonprovisional patent application Ser. No. 13/625,628, filed Sep. 24, 2012, the entirety of which is incorporated herein by reference.

TECHNICAL FIELD

Embodiments include methods and systems for facilitating computations of physiological characteristics. More specifically, embodiments include methods and systems for processing computer models to facilitate computations.

BACKGROUND

Modeling physiological characteristics in a human or animal patient may be useful in a number of different situations. For example, modeling coronary artery blood flows, pressures and other characteristics may be used for assessing coronary artery disease and evaluating treatment options. Various embodiments of a noninvasive method and system for providing such physiological modeling are described, for example, in U.S. patent application Ser. No. 13/013,561, filed Jan. 25, 2011, and entitled "Method and System for Patient-Specific Modeling of Blood Flow," which is incorporated herein by reference in its entirety.

Using computation fluid dynamics and three-dimensional models of various portions of a patient's anatomy to generate physiological measurements from noninvasively generated patient-specific data is a complex process. In order to be useful in assessing a patient's disease and evaluating treatment options, the computer models generated by such a process must be sufficiently detailed to be accurate. At the same time, if the models are too detailed, they may require unrealistic amounts of computing power and/or take impractical amounts of time to create. For example, in modeling the coronary arteries to assess blood pressures and/or blood flows, as might be used in assessing the need for an intervention such as placement of a stent or bypass graft, computer models must be sufficiently detailed to allow for computation of blood flow and/or blood pressure. At the same time, to be useful, these computations must be provided to a physician in a reasonable amount of time and must still be accurate.

Thus, a need exists for a method and system for assessing coronary anatomy, myocardial perfusion, and coronary artery flow noninvasively. Such a method and system must be sufficiently accurate to promote confidence in the assessment of the patient's physiology. At the same time, the method and system needs to be practical from the standpoint of the time required to provide the physiological data and the computing power required to do so.

The foregoing general description and the following detailed description are exemplary and explanatory only and are not restrictive of the disclosure.

SUMMARY

In one aspect, a system for noninvasively determining at least one physiological characteristic of a patient may include at least one computer system configured to: using a three-dimensional surface mesh model created using patient-specific imaging data, create a three-dimensional combined surface and volume mesh model, including at least a first model portion that has a different spatial resolution than at least a second model portion; input the three-dimensional surface and volume mesh model into a fluid simulation system; and determine a measurement of the physiological characteristic, using the fluid simulation system.

In some embodiments, the computer system may be configured to create the three-dimensional combined surface and volume model by identifying at least a first portion of the surface mesh model as having a first level of complexity, identifying at least a second portion of the surface mesh model as having a second level of complexity that is less than the first level, and creating the surface and volume mesh model such that it includes at least one high-resolution portion related to the first portion of the surface model and at least one low-resolution portion related to the second portion of the surface model. In one embodiment, the high-resolution portion may include mesh elements that are smaller than mesh elements of the low-resolution portion. In one embodiment, identifying the first and second portions may involve identifying first and second patterns of blood flow in a coronary artery, where one of the patterns of blood flow is more complex than the other.

In some embodiments, the computer system may be configured to create the three-dimensional combined surface and volume mesh model by forming multiple elongated shaped elements of the surface and volume mesh model along a direction of fluid flow through the surface and volume mesh model, where the first model portion includes shaped elements that are elongated relative to shaped elements of the second model portion. For example, in one embodiment, the shaped elements may be tetrahedrons.

In some embodiments, the computer system may be configured to create the three-dimensional combined surface and volume mesh model by estimating, using the computer system and the surface mesh model, a solution to at least one equation. In some embodiments, the computer system may be further configured to estimate, using the surface and volume mesh model, a solution to at least one equation, before determining the measurement, wherein the solution is input into the fluid simulation system along with the surface and volume mesh model. In some embodiments, the surface and volume mesh model may include separate surface and volume mesh models.

In some embodiments, the computer system may be configured to provide data for use by the fluid simulation system in determining the measurement. For example, the data may include, but is not limited to, surface and volume mesh coordinates, surface and volume element connectivities, model inlet and outlet coordinates and connectivities, and boundary and initial conditions.

In some embodiments, the surface model and the surface and volume mesh model may represent at least a portion of multiple coronary arteries emanating from a portion of an aorta. In some embodiments, the physiological characteristic may be fractional flow reserve.

In another aspect, a method for noninvasively determining at least one physiological characteristic of a patient using a computer system may involve: creating, using the computer system and the three-dimensional surface mesh model created using patient-specific imaging data, a three-dimensional combined surface and volume mesh model, including at least a first model portion that has a different spatial resolution than at least a second model portion; processing the surface and volume mesh model to generate a refined surface and volume mesh model; inputting the refined surface and volume mesh model into a fluid simulation system of the computer system; and determining a measurement of the physiological characteristic, using the fluid simulation system and based on the refined surface and volume mesh model.

In some embodiments, creating the combined surface and mesh model may include: identifying a high-complexity portion of the surface mesh model; identifying a low-complexity portion of the surface mesh model; and creating the surface and volume mesh model such that the first model portion comprises a high-resolution portion related to the high-complexity portion of the surface mesh model and the second model portion comprises a low-resolution portion related to the low-complexity portion of the surface mesh model. In some embodiments, the method may further involve processing the surface mesh model before the identifying steps to generate a refined surface mesh model, where the identifying steps are then performed on the refined surface mesh model. In some embodiments, creating the combined surface and mesh model may involve elongating multiple elements of the surface and volume mesh model along a direction of fluid flow through the surface and volume mesh model, where the first model portion includes elements elongated relative to the second model portion.

In some embodiments, the method may further include, after creating the surface and volume mesh model, generating at least one solution to at least one equation based on the surface and volume mesh model, and using linear interpolation to project the at least one solution onto the surface and mesh model. Optionally, such embodiments may further include processing the surface and volume mesh model to generate a refined surface and mesh model, where the step of using linear interpolation to project the solution is performed on the refined surface and volume mesh model.

In some embodiments, creating the surface and mesh model may involve identifying multiple mesh points that will be refined during the method, where the identified mesh points reside in portions of the surface and mesh model that are more complex than other portions of the surface and mesh model. For example, identifying the mesh points may involve determining whether each of the mesh points is in or near a stenosed vessel of the surface and mesh model, and the method may further involve prescribing a local mesh element size based on a minimum cross-sectional area of the stenosed vessel. As another example, identifying the mesh points may involve determining whether each of the mesh points is in or near an ostium of a coronary artery of the surface and mesh model by determining if each of the mesh points is within a predetermined distance from a centerline point of the surface and volume model located in the ostium. Optionally, such embodiments may further involve setting a mesh element size based on whether the mesh points are in or near the ostium.

In some embodiments, the method may further include, before the inputting step, generating at least one solution to at least one equation, based on the combined surface and volume mesh model, wherein the inputting step further comprises inputting the at least one solution into the fluid simulation system. As mentioned previously, in some embodiments, the surface model and the surface and volume model may represent at least a portion of multiple coronary arteries emanating from a portion of an aorta, and determining the measurement may involve determining a fractional flow reserve.

In another aspect non-transitory computer readable medium may be configured for use on at least one computer system, containing computer-executable programming instructions for performing a method for noninvasively determining at least one physiological characteristic of a patient. The method may involve: creating, using the computer system and the three-dimensional surface mesh model created using patient-specific imaging data, a three-dimensional combined surface and volume mesh model, including at least a first model portion that has a different spatial resolution than at least a second model portion; generating at least one solution to at least one equation, based on the combined surface and volume mesh model; inputting the combined surface and volume mesh model and the at least one solution into a fluid simulation system of the computer system; and determining a measurement of the physiological characteristic, using the fluid simulation system and based on the combined surface and volume mesh model and the at least one solution.

In some embodiments, creating the surface and mesh model may involve identifying multiple mesh points that will be refined during the method, where the identified mesh points reside in portions of the surface and mesh model that are more complex than other portions of the surface and mesh model. For example, in some embodiments, identifying the mesh points may include reading a model geometry of the surface and volume mesh model and solution information computed by the computer system and generating estimates of solution errors for each of the mesh points. In such embodiments, identifying the mesh points may optionally further involve: based on the solution errors, determining a desired mesh size for the surface and volume mesh at each of the mesh points, where the desired mesh size is configured to achieve a solution error that is approximately uniform at approximately all mesh points; and based on the desired mesh sizes, identifying the mesh points that will be refined.

Additional embodiments and advantages will be set forth in part in the description which follows, and in part will be obvious from the description, or may be learned by practice of the disclosure. The embodiments and advantages will be realized and attained by means of the elements and combinations particularly pointed out below.

BRIEF DESCRIPTION OF THE DRAWINGS

The accompanying drawings, which are incorporated in and constitute a part of this specification, illustrate several embodiments and together with the description, serve to explain the principles of the disclosure.

DESCRIPTION OF THE EMBODIMENTS

Reference will now be made in detail to exemplary embodiments, examples of which are illustrated in the accompanying drawings. Wherever possible, the same reference numbers will be used throughout the drawings to refer to the same or like parts.

In an exemplary embodiment, a method and system may determine information relating to blood flow in a specific patient using information retrieved from the patient noninvasively. In some embodiments, the information determined by the method and system may relate to blood flow in the patient's coronary vasculature. Alternatively, the determined information may relate to blood flow in other areas of the patient's vasculature, such as carotid, peripheral, abdominal, renal, and cerebral vasculature.

Figure 3:
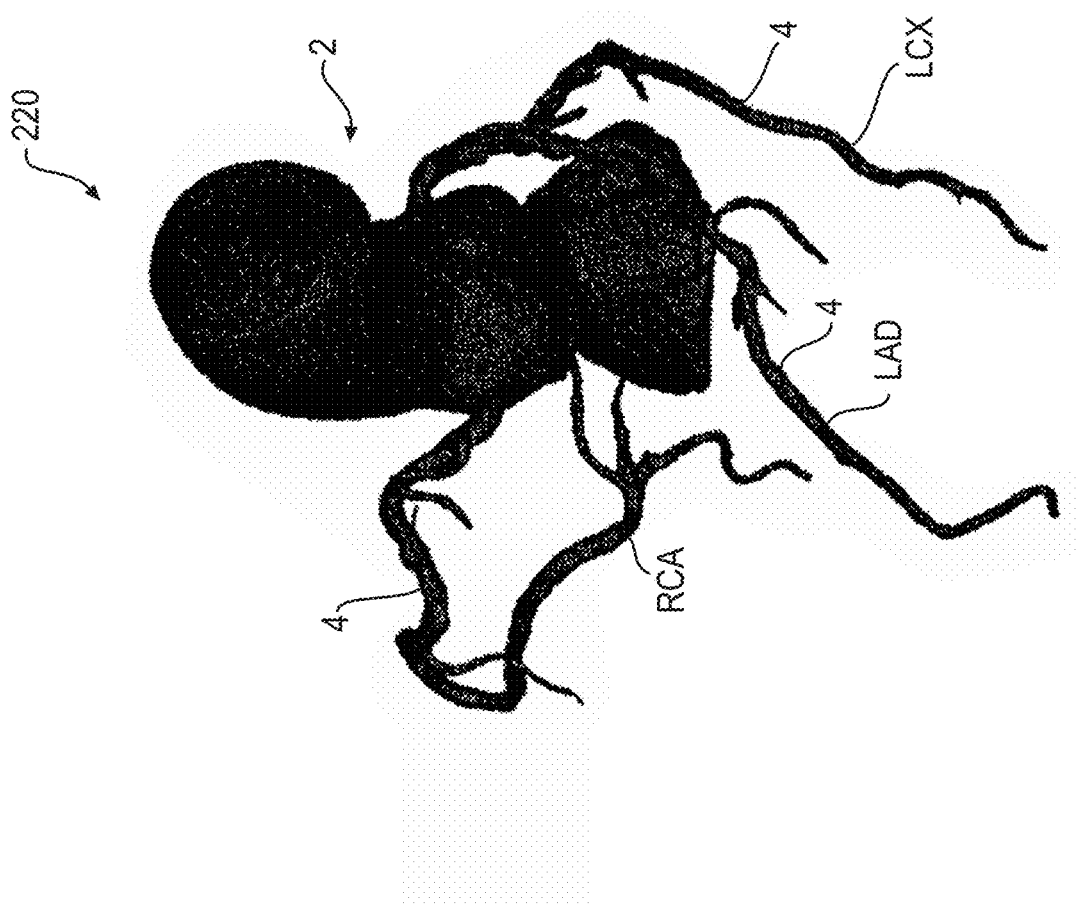
FIG. 3 shows an exemplary three-dimensional model generated using noninvasively obtained imaging data.

Referring to FIG. 3, an example of a three-dimensional computer-generated model 220 of a portion of an aorta 2 and coronary arteries 4 branching from the aorta 2 is provided. The coronary vasculature includes a complex network of vessels, ranging from large arteries to arterioles, capillaries, venules, veins, etc. The coronary vasculature circulates blood to and within the heart and includes the aorta 2, which supplies blood to multiple main coronary arteries 4 (e.g., the left anterior descending (LAD) artery, the left circumflex (LCX) artery, the right coronary (RCA) artery, etc.), which may further divide into branches of arteries or other types of vessels downstream from the aorta 2 and the main coronary arteries 4. Thus, the exemplary method and system may determine information relating to blood flow within the aorta, the main coronary arteries, and/or other coronary arteries or vessels downstream from the main coronary arteries. Although the aorta and coronary arteries (and the branches that extend therefrom) are discussed below, the disclosed method and system may also apply to other types of vessels.

In an exemplary embodiment, the information determined by the disclosed methods and systems may include, but is not limited to, various blood flow characteristics or parameters, such as blood flow velocity, pressure (or a ratio thereof), flow rate, and FFR at various locations in the aorta, the main coronary arteries, and/or other coronary arteries or vessels downstream from the main coronary arteries. This information may be used to determine whether a lesion is functionally significant and/or whether to treat the lesion. This information may be determined using information obtained noninvasively from the patient. As a result, the decision whether to treat a lesion may be made without the cost and risk associated with invasive procedures.

Figure 1:
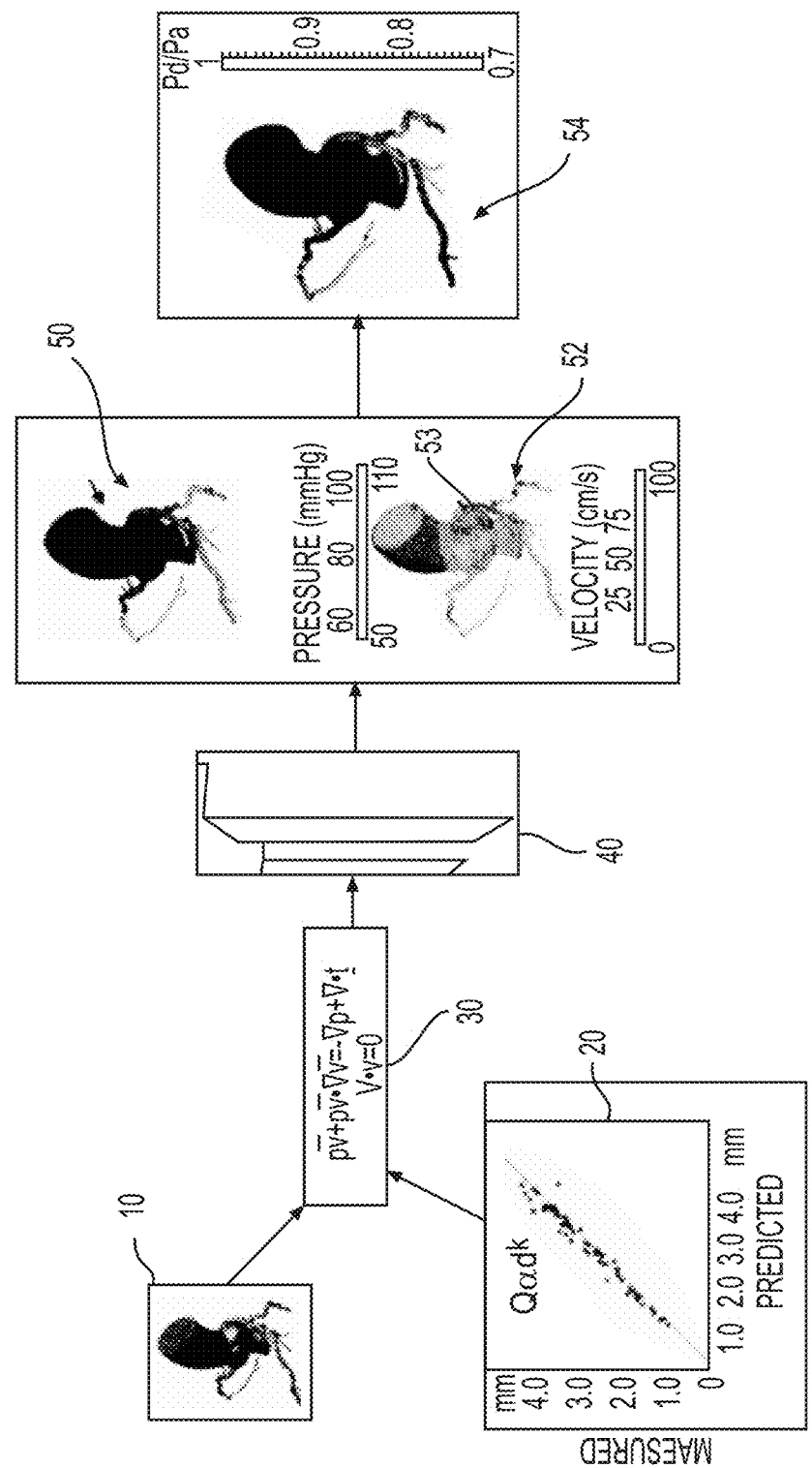
FIG. 1 is a schematic diagram of a system for providing information relating to coronary blood flow in a specific patient, according to an exemplary embodiment.

FIG. 1 shows aspects of a system for providing information relating to coronary blood flow in a specific patient, according to an exemplary embodiment. A three-dimensional model 10 of the patient's anatomy may be created using data obtained noninvasively from the patient as will be described below in more detail. Other patient-specific information may also be obtained noninvasively. In an exemplary embodiment, the portion of the patient's anatomy that is represented by the three-dimensional model 10 may include at least a portion of the aorta and a proximal portion of the main coronary arteries (and the branches extending or emanating therefrom) connected to the aorta.

Various physiological laws or relationships 20 relating to coronary blood flow may be deduced, e.g., from experimental data as will be described below in more detail. Using the three-dimensional anatomical model 10 and the deduced physiological laws 20, multiple equations 30 relating to coronary blood flow may be determined as will be described below in more detail. For example, the equations 30 may be determined and solved using any numerical method, e.g., finite difference, finite volume, spectral, lattice Boltzmann, particle-based, level set, finite element methods, etc. The equations 30 may be solvable to determine information (e.g., pressure, velocity, FFR, etc.) about the coronary blood flow in the patient's anatomy at various points in the anatomy represented by the model 10.

The equations 30 may be solved using a computer 40. Based on the solved equations, the computer 40 may output one or more images or simulations indicating information relating to the blood flow in the patient's anatomy represented by the model 10. For example, the image(s) may include a simulated blood pressure model 50, a simulated blood flow or velocity model 52, a computed FFR (FFRct) model 54, etc., as will be described in further detail below. The simulated blood pressure model 50, the simulated blood flow model 52, and the FFRct model 54 provide information regarding the respective pressure, velocity, and FFRct at various locations along three dimensions in the patient's anatomy represented by the model 10. FFRct may be calculated as the ratio of the blood pressure at a particular location in the model 10 divided by the blood pressure in the aorta, e.g., at the inflow boundary of the model 10, under conditions of increased coronary blood flow, e.g., conventionally induced by intravenous administration of adenosine.

In an exemplary embodiment, the computer 40 may include one or more non-transitory computer-readable storage devices that store instructions that, when executed by a processor, computer system, etc., may perform any of the actions described herein for providing information relating to blood flow in the patient. The computer 40 may include a desktop or portable computer, a workstation, a server, a personal digital assistant, or any other computer system. The computer 40 may include a processor, a read-only memory (ROM), a random access memory (RAM), an input/output (I/O) adapter for connecting peripheral devices (e.g., an input device, output device, storage device, etc.), a user interface adapter for connecting input devices such as a keyboard, a mouse, a touch screen, a voice input, and/or other devices, a communications adapter for connecting the computer 40 to a network, a display adapter for connecting the computer 40 to a display, etc. For example, the display may be used to display the three-dimensional model 10 and/or any images generated by solving the equations 30, such as the simulated blood pressure model 50, the simulated blood flow model 52, and/or the FFRct model 54.

Figure 2:
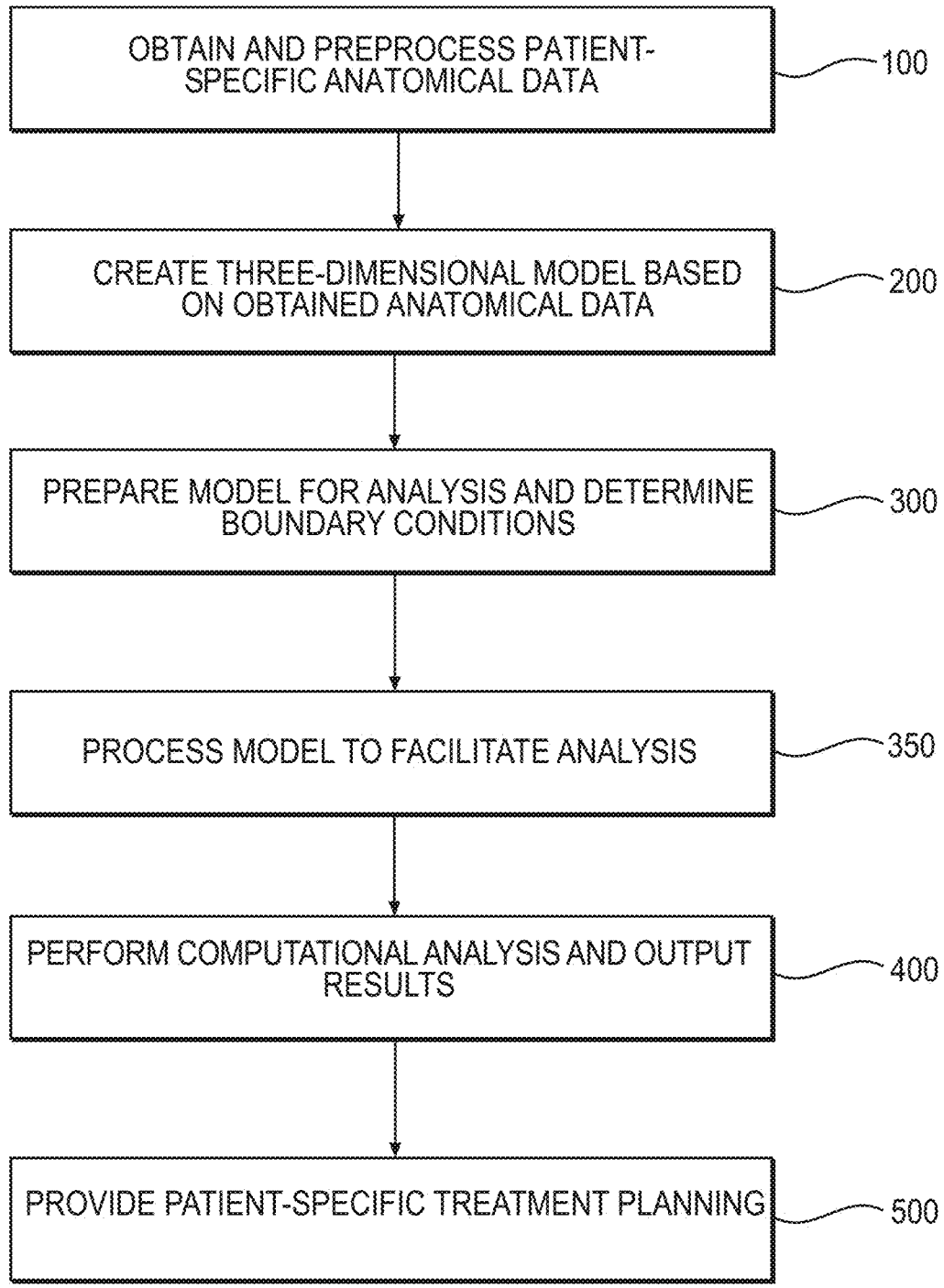
FIG. 2 is a flow chart of a method for providing information relating to blood flow in a specific patient, according to an exemplary embodiment.

FIG. 2 shows aspects of a method for providing information relating to blood flow in a specific patient, according to another exemplary embodiment. The method may include obtaining patient-specific anatomical data, such as information regarding the patient's anatomy (e.g., at least a portion of the aorta and a proximal portion of the main coronary arteries (and the branches extending therefrom) connected to the aorta), and preprocessing the data (step 100). The patient-specific anatomical data may be obtained noninvasively, e.g., by CCTA.

A three-dimensional model of the patient's anatomy may be created based on the obtained anatomical data (step 200). For example, the three-dimensional model may be the three-dimensional model 10 of the patient's anatomy described above in connection with FIG. 1.

The three-dimensional model may be prepared for analysis and boundary conditions may be determined (step 300). For example, the three-dimensional model 10 of the patient's anatomy described above in connection with FIG. 1 may be trimmed and discretized into a volumetric mesh, e.g., a finite element or finite volume mesh. The mathematical equations 30 described above in connection with FIG. 1 may be solved using the volumetric mesh.

Boundary conditions may also be assigned and incorporated into the equations 30 described above in connection with FIG. 1. The boundary conditions provide information about the three-dimensional model 10 at its boundaries, e.g., inflow boundaries, outflow boundaries, vessel wall boundaries, etc. The inflow boundaries may include the boundaries through which flow is directed into the anatomy of the three-dimensional model, such as at an inlet of the aorta near the aortic root. Each inflow boundary may be assigned, e.g., with a prescribed value or field for velocity, flow rate, pressure, or other characteristic, by coupling a heart model and/or a lumped parameter model to the boundary, etc. The outflow boundaries may include the boundaries through which flow is directed outward from the anatomy of the three-dimensional model, such as at an outlet of the aorta near the aortic arch, and the downstream ends of the main coronary arteries and the branches that extend therefrom. Each outflow boundary can be assigned, e.g., by coupling a lumped parameter or distributed (e.g., a one-dimensional wave propagation) model. The prescribed values for the inflow and/or outflow boundary conditions may be determined by noninvasively measuring physiologic characteristics of the patient, such as, but not limited to, cardiac output (the volume of blood flow from the heart), blood pressure, myocardial mass, etc. The vessel wall boundaries may include the physical boundaries of the aorta, the main coronary arteries, and/or other coronary arteries or vessels of the three-dimensional model 10. IN various embodiments, the vessel walls may be represented using a variety of mathematical models, such as but not limited to rigid walls with no-slip (i.e., zero velocity) boundary conditions, deformable walls (e.g., elastically deformable), and/or the like.

As described in greater detail below, the prepared three-dimensional model 10 may be processed (step 350) to facilitate the computational analysis performed in the following step 400. This additional processing step 350 may make the computational analysis of step 400 more accurate and/or may reduce the time and/or computing power required for the analysis. In some embodiments, the step of preparing the model for analysis 300 and the step of further processing the model 350 may be combined, and in use these "steps" may flow together and be performed so quickly and automatically that they are not discernible as discrete steps. Therefore, the description of the discrete steps 300 and 350 is provided herein for ease of description only and should not be interpreted as a requirement of discrete and separate steps in every embodiment. Again, the advantage provided by the processing step 350 is that, by processing the model created in step 300, subsequent analysis (step 400) can be performed more quickly, more accurately and/or with less computing power. This advantage may be quite significant in an overall process as complex as the one described in the present application.

The computational analysis may be performed using the prepared and processed three-dimensional model and the determined boundary conditions (step 400) to determine blood flow information for the patient. For example, the computational analysis may be performed with the equations 30 and using the computer 40 described above in connection with FIG. 1 to produce the images described above in connection with FIG. 1, such as the simulated blood pressure model 50, the simulated blood flow model 52, and/or the FFRct model 54.

The method may also include providing patient-specific treatment options using the results (step 500). For example, the three-dimensional model 10 created in step 200 and/or the boundary conditions assigned in step 300 may be adjusted to model one or more treatments, e.g., placing a coronary stent in one of the coronary arteries represented in the three-dimensional model 10 or other treatment options. Then, the computational analysis may be performed as described above in step 400 in order to produce new images, such as updated versions of the blood pressure model 50, the blood flow model 52, and/or the FFRct model 54. These new images may be used to determine a change in blood flow velocity and pressure if the treatment option(s) are adopted.

Steps 100, 200, 300, 400 and 500 are described in significant detail in U.S. patent application Ser. No. 13/013, 561, which was previously incorporated herein by reference. Therefore, these steps are not described in detail in the present application. Step 350 is described in further detail below.

The systems and methods disclosed herein may be incorporated into a software tool accessed by physicians to provide a noninvasive means to quantify blood flow in the coronary arteries and to assess the functional significance of coronary artery disease. In addition, physicians may use the software tool to predict the effect of medical, interventional, and/or surgical treatments on coronary artery blood flow. The software tool may prevent, diagnose, manage, and/or treat disease in other portions of the cardiovascular system including arteries of the neck (e.g., carotid arteries), arteries in the head (e.g., cerebral arteries), arteries in the thorax, arteries in the abdomen (e.g., the abdominal aorta and its branches), arteries in the arms, or arteries in the legs (e.g., the femoral and popliteal arteries). The software tool may be interactive to enable physicians to develop optimal personalized therapies for patients.

For example, the software tool may be incorporated at least partially into a computer system, e.g., the computer 40 shown in FIG. 1 used by a physician or other user. The computer system may receive data obtained noninvasively from the patient (e.g., data used to create the three-dimensional model 10, data used to apply boundary conditions or perform the computational analysis, etc.). For example, the data may be input by the physician or may be received from another source capable of accessing and providing such data, such as a radiology or other medical lab. The data may be transmitted via a network or other system for communicating the data, or directly into the computer system. The software tool may use the data to produce and display the three-dimensional model 10 or other models/meshes and/or any simulations or other results determined by solving the equations 30 described above in connection with FIG. 1, such as the simulated blood pressure model 50, the simulated blood flow model 52, and/or the FFRct model 54. Thus, the software tool may perform steps 100-500. In step 500, the physician may provide further inputs to the computer system to select possible treatment options, and the computer system may display to the physician new simulations based on the selected possible treatment options. Further, each of steps 100-500 shown in FIG. 2 may be performed using separate software packages or modules.

Alternatively, the software tool may be provided as part of a web-based service or other service, e.g., a service provided by an entity that is separate from the physician. The service provider may, for example, operate the web-based service and may provide a web portal or other web-based application (e.g., run on a server or other computer system operated by the service provider) that is accessible to physicians or other users via a network or other methods of communicating data between computer systems. For example, the data obtained noninvasively from the patient may be provided to the service provider, and the service provider may use the data to produce the three-dimensional model 10 or other models/meshes and/or any simulations or other results determined by solving the equations 30 described above in connection with FIG. 1, such as the simulated blood pressure model 50, the simulated blood flow model 52, and/or the FFRct model 54. Then, the web-based service may transmit information relating to the three-dimensional model 10 or other models/meshes and/or the simulations so that the three-dimensional model 10 and/or the simulations may be displayed to the physician on the physician's computer system. Thus, the web-based service may perform steps 100-500 and any other steps described below for providing patient-specific information. In step 500, the physician may provide further inputs, e.g., to select possible treatment options or make other adjustments to the computational analysis, and the inputs may be transmitted to the computer system operated by the service provider (e.g., via the web portal). The web-based service may produce new simulations or other results based on the selected possible treatment options, and may communicate information relating to the new simulations back to the physician so that the new simulations may be displayed to the physician.

One or more of the steps described herein may be performed by one or more human operators (e.g., a cardiologist or other physician, the patient, an employee of the service provider providing the web-based service or other service provided by a third party, other user, etc.), or one or more computer systems used by such human operator(s), such as a desktop or portable computer, a workstation, a server, a personal digital assistant, etc. The computer system(s) may be connected via a network or other method of communicating data.

With continued reference to FIG. 2, as mentioned above, in some embodiments, the three-dimensional model provided in step 300 may be processed in step 350 to facilitate computational analysis and generation of results (step 400). This further processing step 350, which in alternative embodiments may be combined with step 300, will now be described in greater detail.

In general, the further processing step 350 involves using variable spatial resolution for patient-specific mathematical modeling, such as modeling of fluid mechanics, solid mechanics, fluid-structure interaction and/or the like. Variable spatial resolution is used to process the model generated by step 300 of the method to effectively initialize the equations used in step 400 to model the physiological characteristic(s) or measurement(s) of interest. In general, a computer generated, unrefined surface mesh is the output of step 300, and a refined mesh is the output of step 350. Typically, the refined mesh includes surface and volume mesh data and allows for more effective initialization of the analysis performed in step 400. The process of step 350 is performed by a computer system, including computer software configured to perform operations in sequence or in parallel.

For exemplary purposes, the system used to perform step 350 may be referred to herein as "the presolver," and the system used to perform step 400 may be referred to herein as "the solver." The presolver generally refines the model of step 300 to prepare it for computational analysis by the solver (step 400). In some embodiments, the presolver and the solver may run at the same time for a given set of patient-specific data. Furthermore, in some embodiments, data from the presolver may be output into the solver, processed, and provided back to the presolver during step 350. In other words, step 350 may include functionality of both the presolver and the solver. Thus, the terms "presolver" and "solver" are used primarily for ease of description and should not be interpreted as limiting the scope of the embodiments to any specific order of steps or operations.

At a high level, the presolver (step 350) converts a surface representation (surface mesh with centerlines) of a physiologic geometry into a specialized computational mesh that discretizes the surface and volume of the geometry. The surface and volume meshes (also referred to at the "surface and volume mesh model" or "combined surface and volume mesh model") accurately represent the underlying geometry of the patient's anatomy and are suitable for rapidly solving equations throughout the entire computational domain. In addition, step 350 prepares specialized pressure and velocity fields that initialize the mathematical equation solver (step 400) in order to accelerate solver convergence and increase solver performance. In a typical embodiment, the input into step 350 is a surface mesh model, with centerlines, of the relevant physiology and one or more patient-specific physiologic parameters, such as but not limited to blood pressure, patient height, patient weight and myocardial mass. The outputs from step 350 into step 400 are specialized surface and volume meshes and an initial solution field used to rapidly and accurately solve mathematical equations on the computational domain. Generally, step 350 is fully automated and performs one or more sequences of operations. Due to the automation, however, all of the sequences of operations described below will typically be transparent to the user of the overall system.

According to one embodiment, the method described by step 350 may involve: (1) using a three-dimensional surface mesh model created using patient-specific imaging data to create a three-dimensional combined surface and volume mesh model, including at least a first model portion that has a different spatial resolution than at least a second model portion; and (2) inputting the three-dimensional surface and volume mesh model into a fluid simulation system. The fluid simulation system, in step 400, then performs computational analysis and generates results. In some embodiments, method step 350 may include additional sub-steps. For example, in some embodiments, the three-dimensional surface mesh model that is the input into step 350 may be processed to provide a refined surface mesh model, which is then used to create the combined surface and volume mesh model. In some embodiments, the surface and volume mesh model may be processed to generate a refined surface and mesh model, and that refined surface and volume mesh model may be input into the fluid simulation system. In some embodiments, one or more solutions to one or more equations may be produced as part of step 350, and the solutions may be used to refine the surface and volume mesh model and/or may be input into the fluid simulation system. Thus, step 350 may include any of a number of suitable sub-steps, which will be described further below.

Figure 4A:
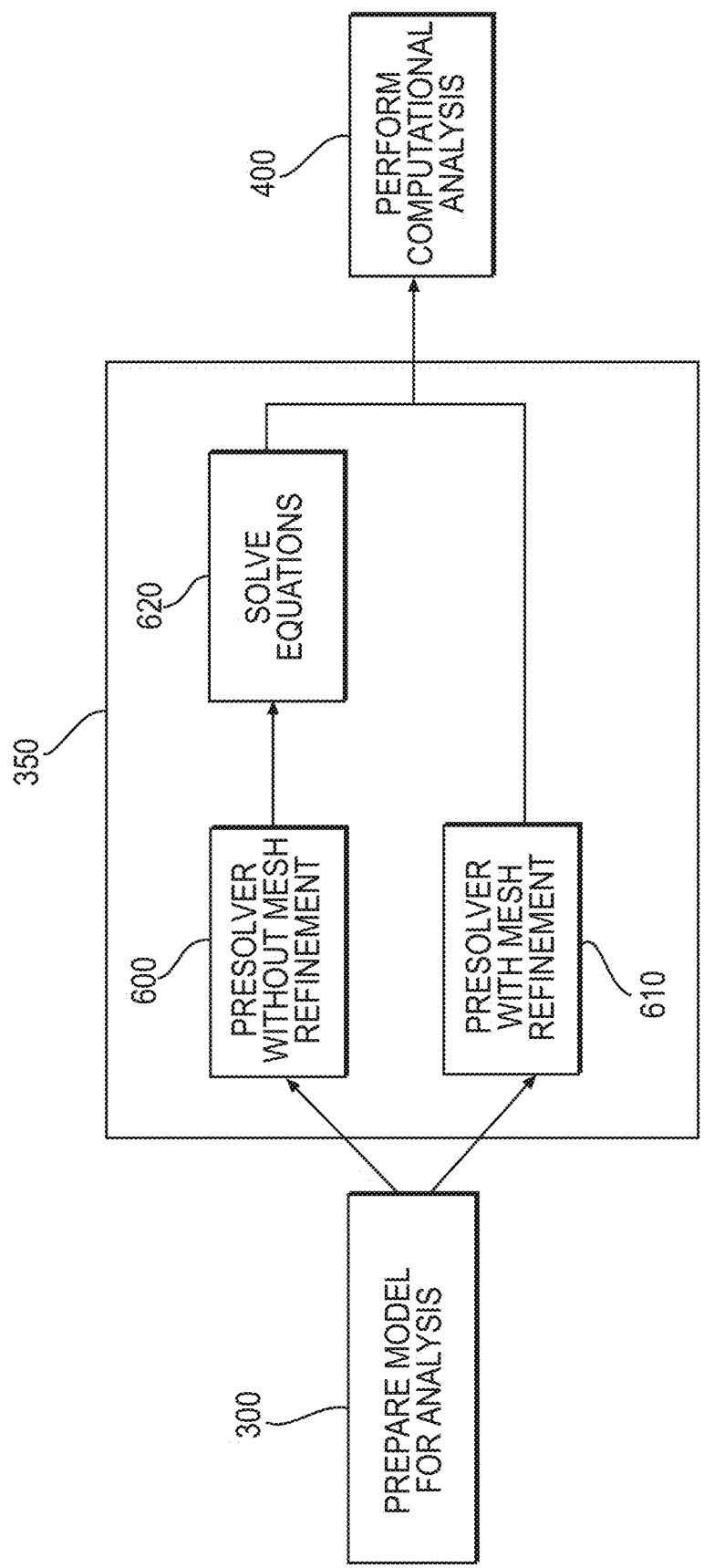
FIG. 4A is a flow chart of a portion of the method illustrated in FIG. 2, according to an exemplary embodiment.
Figure 4B:
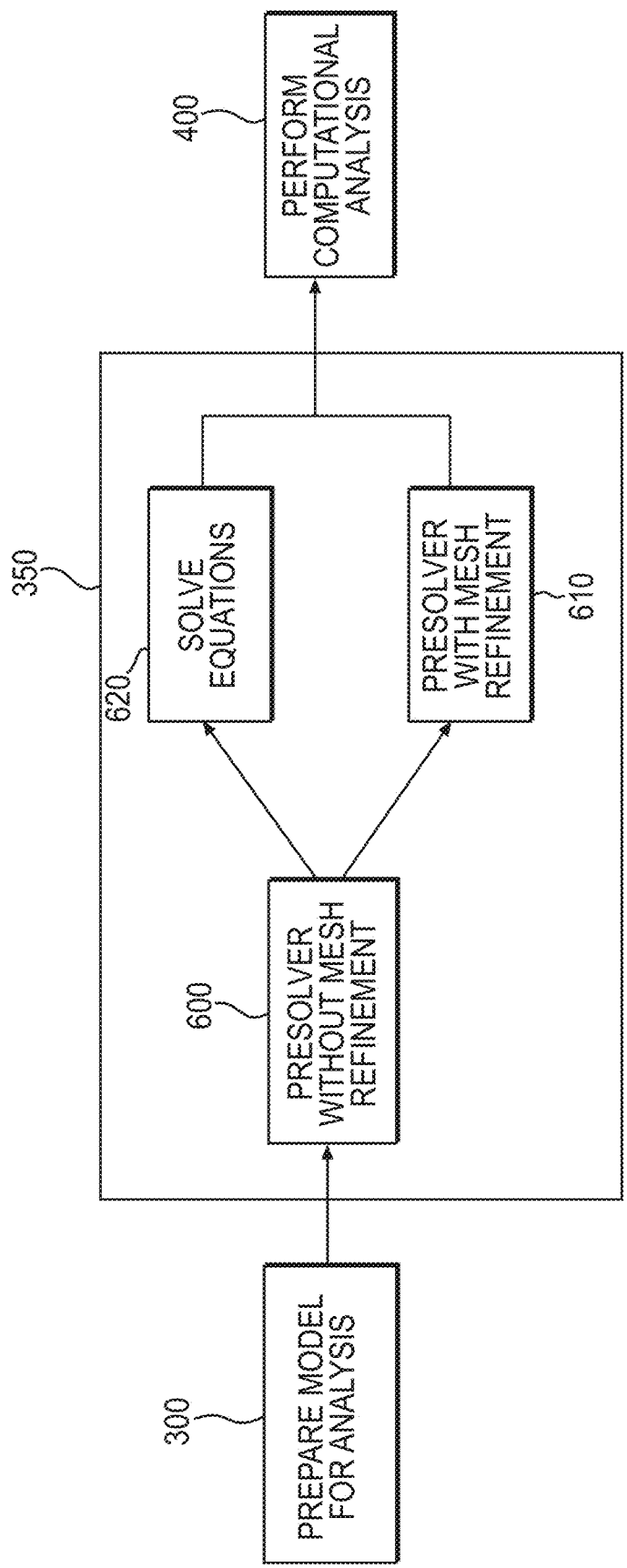
FIG. 4B is a flow chart of a portion of the method illustrated in FIG. 2, according to an alternative exemplary embodiment.
Figure 4C:
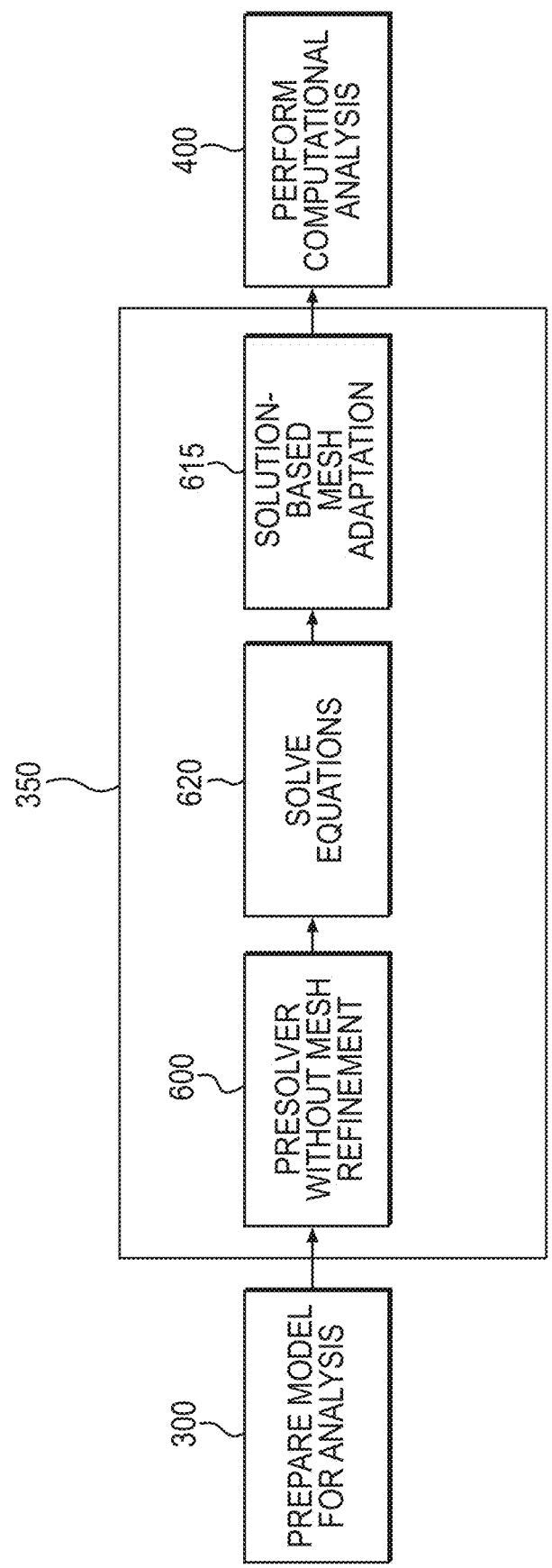
FIG. 4C is a flow chart of a portion of the method illustrated in FIG. 2, according to another alternative exemplary embodiment.

Referring now to FIGS. 4A-4C, the model processing step 350 may include a number of different sequences of operations performed in one of a number of different orders, according to various embodiments. In some embodiments, two or more sequences may be performed concurrently (FIGS. 4A and 4B), while in alternative embodiments, all sequences may be performed sequentially (FIG. 4C). Referring to FIG. 4A, for example, in one concurrent mode, the unrefined surface mesh model of step 300 may be fed into a first operational sequence 600, referred to as "presolver without mesh refinement," and a third operational sequence 610, referred to as "presolver with mesh refinement." First and third operational sequences 600, 610, which are independent from one another, may be started at the same time or approximately the same time. These two sequences 600, 610 generate separate surface/volume meshes without and with refinement, respectively. When sequence 600 completes (i.e., the mesh without refinement is generated), a second operational sequence 620 may be started (i.e., equations are solved on the mesh without refinement). Note that sequence 620 may be executed despite the possible incompletion of sequence 610. Upon the completion of both sequence 620 and sequence 610, a refined mesh is provided to the solver, for computational analysis step 400.

Referring now to FIG. 4B, in an alternative embodiment, step 350 may involve starting sequence 600 by itself. The resulting mesh from sequence 600 may then be input into sequences 610 and 620 simultaneously. The results of sequences 610 and 620 are then provided to the solver (step 400).

In another alternative embodiment, and with reference now to FIG. 4C, all sequences may be performed successively (i.e., sequentially). In this embodiment, sequence 600 is run to completion, the resulting data are then fed into sequence 620, which is run to completion, the resulting data are then fed into an alternate third sequence 615, referred to as "solution-based mesh adaptation," which is run to completion, and the resulting refined model is then provided to the solver 400. In this embodiment, alternate third sequence 615 is used, rather than sequence 610, since the sequences are run sequentially. It may be possible, in other alternative embodiments, to run the various sequences in other orders or configurations or to add further sequences. The various sequences 600, 610, 615 and 620 will now be described in further detail.

Figure 5:
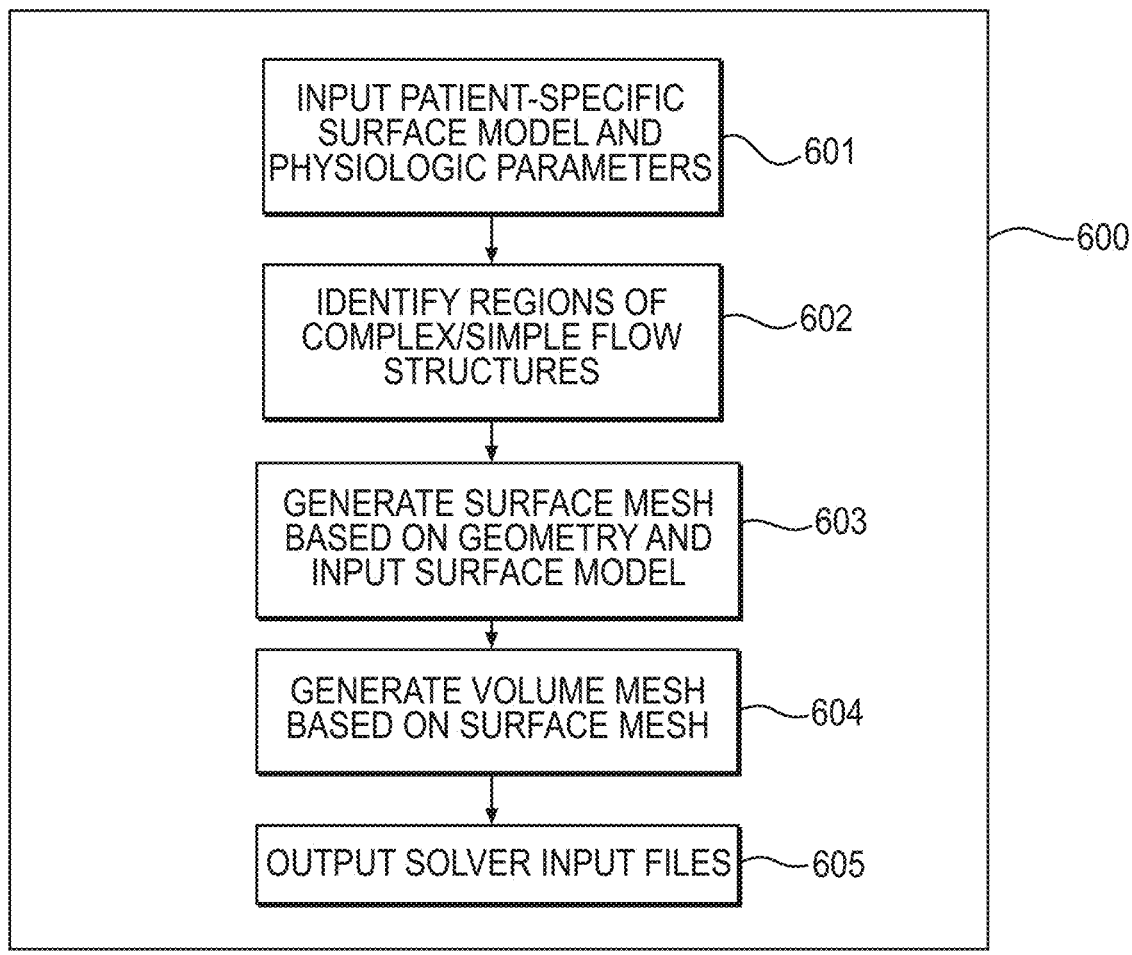
FIG. 5 is a flow chart of substeps of one of the steps of the method illustrated in FIGS. 4A-4C, according to an exemplary embodiment.
Figure 11:
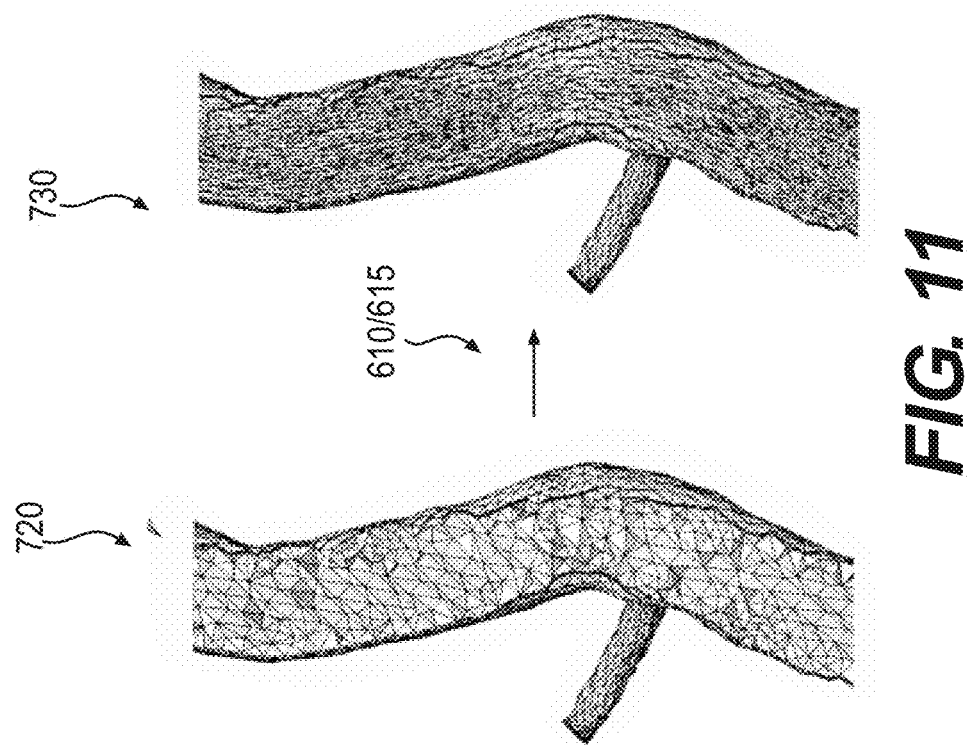
FIG. 11 shows unrefined and refined volume mesh models, according to an exemplary embodiment.
Figure 10:
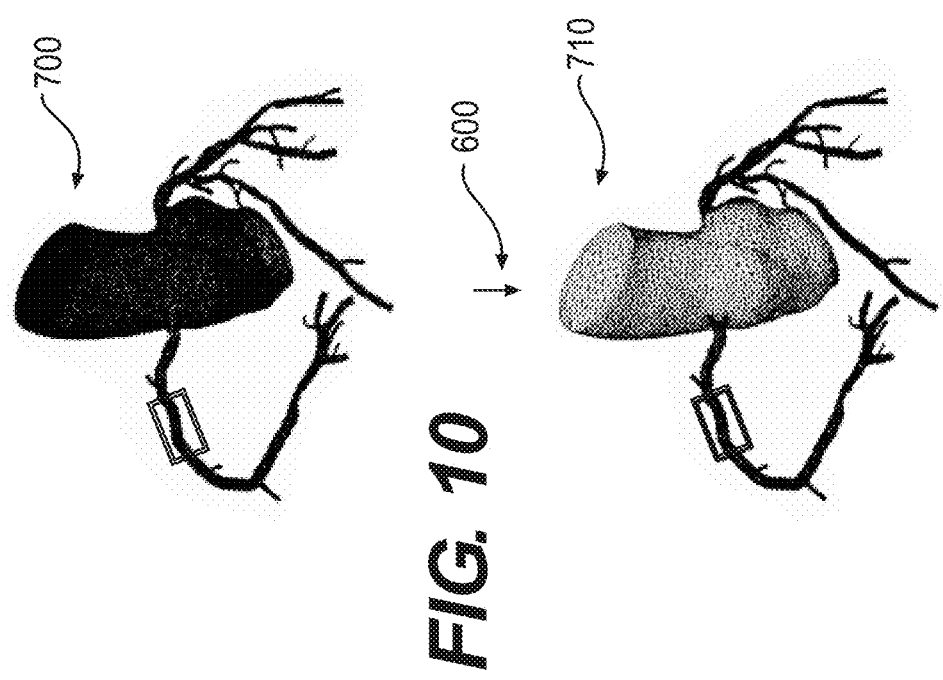
FIG. 10 shows unrefined and refined surface mesh models, according to an exemplary embodiment.

Referring now to FIG. 5, sequence 600 may be referred to as a process of "presolver without mesh refinement." As illustrated in FIG. 10, the input into sequence 600 includes a surface mesh model 700, for example a surface mesh model of a portion of an aorta and coronary arteries branching from the aorta. The output from sequence 600 includes a refined surface mesh 710, as well as a volume mesh 720 (FIG. 11). A first operation 601 of sequence 600 involves inputting the patient-specific surface model 700 (from step 300 of FIG. 2) and physiological parameters into the sequence 600. First operation 601 may initially involve, for a given patient model, reading all required and optional patient-specific parameters. In one embodiment, parameters used for generating the mesh and setting boundary conditions may include, but are not limited to, systolic blood pressure, diastolic blood pressure, patient height, patient weight, myocardial mass, and a name of the input geometry file. Optional additional parameters may include, but are not limited to, patient hematorcrit, number of computer processors on which the mathematical equations will be solved and/or specialized mesh refinement parameters.

First operation 601 may also include initializing presolver data structures and supporting libraries, including third party libraries for parallel computing (e.g., OpenMPI), memory and array management (e.g., boost), input/output streams (e.g., rapidxml), and/or mesh generation (e.g., Simmetrix). Other libraries and functionality, which may be selected based on the software implementation of the presolver, may also be initialized. First operation 601 may also include reading and parsing the surface mesh model (from step 300). The surface mesh model contains a discrete representation of the entire physiologic domain on which the mathematical equations will be solved, and first operation 601 reads the discrete representation of the patient-specific model 700 and stores model information, such as but not limited to surface coordinates, surface element connectivity, centerline points and coordinates, vessel areas and normals at inlet/outlet points, hierarchical information of the centerline tree structure, and boundary information. These data are used to generate the specialized surface and volume meshes and to prepare the initial solution field for solving the equations.

A second operation 602 of sequence 600 may involve identifying and labeling portions of the discrete model that will receive specialized treatment by the presolver. For example, certain regions of a coronary artery may be identified as having relatively complex flow patterns compared to other regions of the artery. Alternatively, or additionally, certain regions of a coronary artery may be identified as having relatively simple flow patterns compared to other regions of the artery. Such regions may be identified during the second operation 602 so that they may be treated differently during processing of the data. Specialized treatment includes any mathematical, geometric or meshing operation that is applied to a localized region of the model and not to the model as a whole. Such operations may include, for example, the generation of relatively high or low resolution meshes in selected regions of the model, smoothing or blending of the model surface(s), and cropping or trimming of the model surface.

A third operation 603 of sequence 600 may involve generating a surface mesh based on the geometry to adequately capture the input surface model. In this operation 603, a meshing library may be used to create a specialized surface mesh that spatially resolves the discrete physiological model. Adequate spatial resolution of the model may comprise a surface mesh that captures the complex morphology of the geometric surface to enable the accurate solution of the equations used to model the physiological phenomena of interest. In one embodiment, the specialized surface mesh may be created by: (1) setting the mesh element sizes on all model inlet and outlet surfaces to be a function of the cross-sectional area of the respective inlet or outlet surface; (2) setting the mesh element size to be relatively large on all portions of the model that contain simple and slowly varying topology, wherein the solutions to the mathematical equations do not require high spatial resolution; (3) setting the mesh element size to be relatively small on all portions of the model that contain complex and rapidly varying topology, wherein the solutions to the mathematical equations require high spatial resolution; and (4) after all mesh element sizes are determined, using a mesh generator to generate the surface mesh with the determined element sizes.

The term "mesh elements" is used generally herein to describe the multiple components or pieces that make up a mesh model. Generally, these elements may take the form of shapes, with typically many of the shapes making up the complete surface and/or volume mesh models. For example, a surface or volume mesh model may be made of multiple polyhedrons, such as tetrahedrons.

Once the surface mesh is generated, the fourth operation 604 of sequence 600 may involve using a meshing library to generate a volume mesh.

Finally, operation 605 of sequence 600 may involve outputting data and information required to solve the equations step 620. Output data from sequence 600 may include, for example, surface and volume mesh coordinates, surface and volume element connectivities, model inlet and outlet coordinates and connectivities, boundary and initial conditions, and geometric model information required for solving the equations. In other words, the output data includes a combined surface and volume mesh without refinement. After operation 605, an optional step (not shown in FIG. 5) may involve cleaning up computer memory and in some instance exiting the presolver (such as when the solver is used to solve the mathematical equations of step 620).

Figure 6:
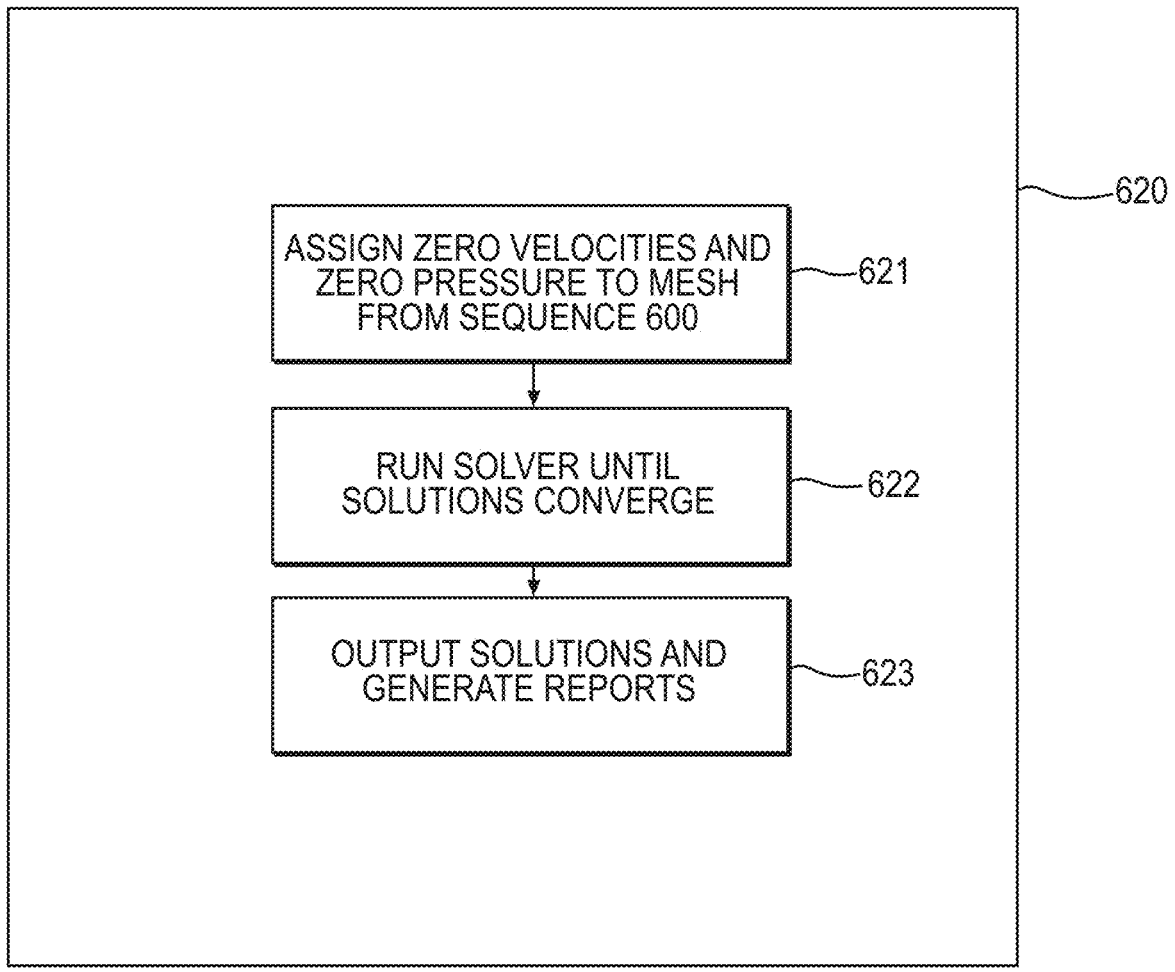
FIG. 6 is a flow chart of substeps of one of the steps of the method illustrated in FIGS. 4A-4C, according to an exemplary embodiment.

With reference now to FIG. 6, after the surface/volume mesh is created in sequence 610, the mesh data is provided to sequence 620. In some embodiments, sequence 620 may be performed by what has been referred to thus far as the solver. In other embodiments, sequence 620 may be performed by software residing outside and separate from the solver. In any case, sequence 620, for the purposes of this description, is considered to be part of the presolver method. Generally, sequence 620 involves solving equations to obtain a solution that meets user-specified accuracy requirements. In one embodiment, sequence 620 may involve a first operation 621 that comprises assigning zero velocities and zero pressure to the mesh from sequence 610. A second operation 622 may then involve running the solver until the solutions converge. Finally, a third operation 623 may involve outputting solutions and/or generating reports, which may be used by a subsequent step in the modeling process. Various additional details regarding solving the equations of sequence 620 are described in detail in U.S. patent application Ser. No. 13/013,561, which was previously incorporated by reference.

Figure 7:
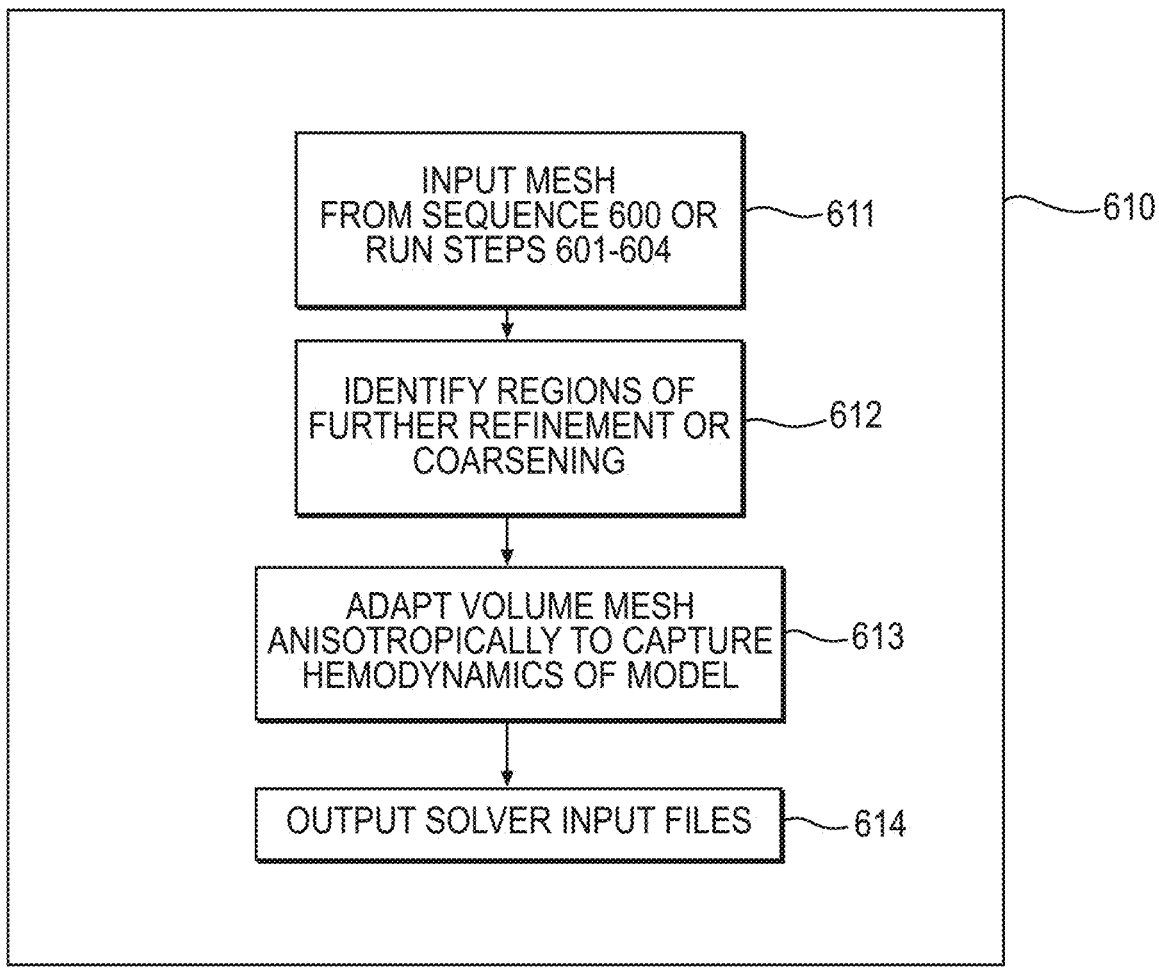
FIG. 7 is a flow chart of substeps of one of the steps of the method illustrated in FIGS. 4A and 4B, according to an exemplary embodiment.

Referring now to FIG. 7, in some embodiments (for example, those illustrated in FIGS. 4A and 4B), the presolver step 350 includes sequence 610, involving applying a presolver with mesh refinement. The first operation 611 of sequence 610 may involve either inputting (or receiving) the mesh from sequence 600 (as in FIG. 4B) or performing operations 601, 602, 603 and 604 of sequence 600 (as in FIG. 4A). The second operation 612 may involve identifying and storing mesh points that should be refined. Mesh points typically should be refined if they lie within regions of the vessel geometry that contain complex solution features that require additional spatial resolution (i.e., mesh elements) to resolve adequately. In one embodiment, for example, presolver mesh refinement may involve the following steps:

(1) Associating each mesh point with its nearest point on the centerline tree of the model;

(2) Identifying and storing all mesh points on the model that contain simple and slowly varying topology, wherein the solutions to the equations do not require high spatial resolution, These mesh points will not be refined. For example, in some embodiments, this step may involve identifying and storing all mesh points inside the aorta, because no complex flow features are expected inside the aorta;

(3) Identifying and storing all mesh points of the model that contain complex or rapidly varying topology, wherein the solutions to the equations require high spatial resolution. These points are marked for mesh refinement;

(4) At the points marked for mesh refinement, determining an appropriate mesh size that accurately captures features of the mathematical solution. A suitable mesh size may be determined by factors such as but not limited to geometric topology of the model, anticipated or computed solution profiles or gradients, modeling constraints, and computer resource constraints. In some embodiments, for example, this step may involve identifying and storing all mesh points inside the coronary arteries that require mesh refinement.

In one exemplary embodiment, the process of identifying and storing mesh points for refinement, for example in the coronary arteries, may include the following steps:

(1) For each centerline point in the coronary tree, determine if the point is in or near a stenosed vessel. A centerline point is in or near a stenosed vessel if at least one of the following conditions is satisfied:
  a. the cross-sectional area of a given centerline point is $<\frac{1}{2}$ the average cross-sectional area of the centerline segment that contains the given point; or
  b. a given centerline point is within a user-specified distance downstream of a centerline point that is identified as being inside a stenosed vessel (2) For each mesh point of the model, determine if the mesh point is in or near a stenosed vessel. In other words, for a given mesh point, determine if the nearest centerline point is in or near a stenosed vessel per the definitions stated above;

(3) If the given mesh point is in or near a stenosed vessel, then prescribe a local mesh size that is based on the minimum cross-sectional area of the stenosed vessel, i.e., the minimum cross-sectional area of the centerline point in the stenosis. Otherwise, prescribe a local element size based on the local cross-sectional area of the vessel, i.e., the cross-sectional area of the nearest centerline point;

(4) Identify and store mesh points that are located in one of the ostia of the coronary arteries (i.e., the openings of the coronary arteries into the aorta). A given mesh point is in an ostium if the point is within a user-specified distance from a centerline point that is in the ostium;

(5) If the given mesh point is in or near an ostium, then ensure the local mesh size is below a user-specified tolerance. The user-specified tolerance is a function of the local cross-sectional area of the vessels. If the mesh size is above the user-specified tolerance, then set the local mesh size to the user-specified tolerance. Otherwise, use the existing local mesh size;

(6) If the given mesh point is not near the ostium (i.e., sufficiently distant from the ostium), then do not modify the local mesh size;

(7) For mesh points that are marked for refinement, set anisotropic size parameters of the mesh elements. Anisotropy parameters (e.g., element skewness or stretching) are based on the cross-sectional area and normal of the vessel as characterized by the area and normal of the nearest centerline point.

The next operation 613 in sequence 610 involves adapting the volume mesh anisotropically to capture the hemodynamics of the model. This operation 613 involves using the meshing library to refine the volume mesh based on the mesh element sizing method described above. In some embodiments, mesh refinement may occur in parallel, so different portions of the mesh are refined using different computer processors to speed up the process of mesh refinement.

The final operation 614 in sequence 610 involves adapting outputting data and information required to solve the mathematical equations of interest. Presolver output data may include, for example, surface and volume mesh coordinates, surface and volume element connectivities, model inlet and outlet coordinates and connectivities, boundary and initial conditions, and geometric model information required to solve the equations. Once sequence 610 is complete, in some embodiments, the method may include cleaning up computer memory, and exiting the presolver.

Figure 8:
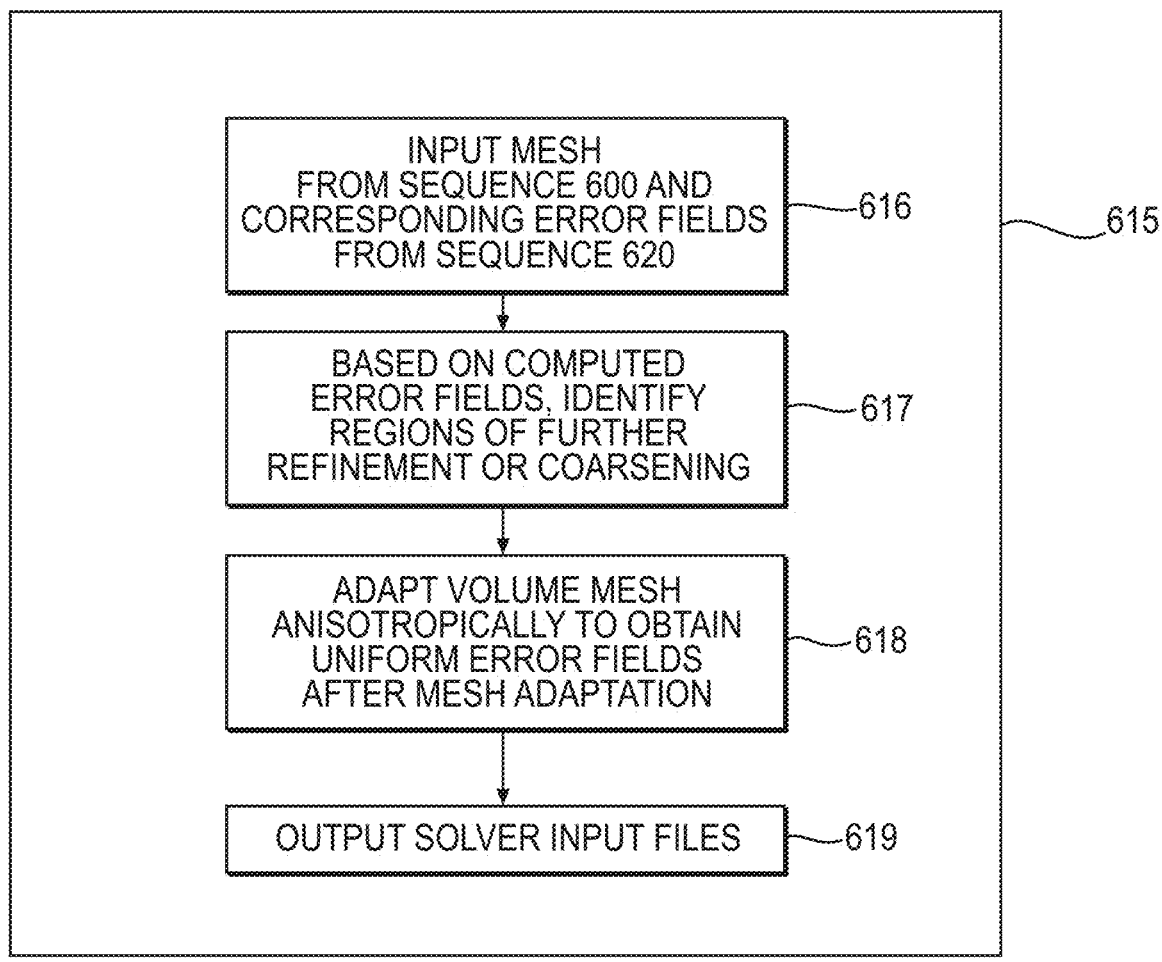
FIG. 8 is a flow chart of substeps of one of the steps of the method illustrated in FIG. 4C, according to an exemplary embodiment.

With reference now to FIG. 8, in some embodiments (such as that illustrated in FIG. 4C), the presolver method may include the sequence 615—a solution-based mesh adaptation. In one embodiment, sequence 615 may include a first operation 616 of inputting (or receiving) the mesh from sequence 600 and the solutions (corresponding error fields) from sequence 620. This operation 616 may include reading the model geometry (of the mesh) from sequence 600 and the solution information computed from sequence 620 and computing estimates of solution errors at each mesh point.

A second operation 617 may involve, based on the solution errors computed above, computing a desired mesh size at every mesh point. The desired mesh size is generally one configured to achieve a solution error that is approximately uniform at all (or approximately all) mesh points. Based on the desired, computed mesh sizes, operation 617 may also include identifying and marking mesh points that require refinement or coarsening.

A third operation 618 may involve adapting the volume mesh anisotropically to obtain uniform error fields after mesh adaptation. Some embodiments may include using a meshing library to refine the volume mesh based on the mesh element sizings determined in step 617. Mesh refinement may occur in parallel, so different portions of the mesh may be refined using different computer processors to speed up the process of mesh refinement.

A fourth operation 619 may involve outputting data and information required to solve the mathematical equations of interest. Presolver output data may include, for example, surface and volume mesh coordinates, surface and volume element connectivities, model inlet and outlet coordinates and connectivities, boundary and initial conditions, and geometric model information for solving the equations. In some embodiments, after the fourth step, the method may include cleaning up computer memory and exiting the presolver.

Figure 9:
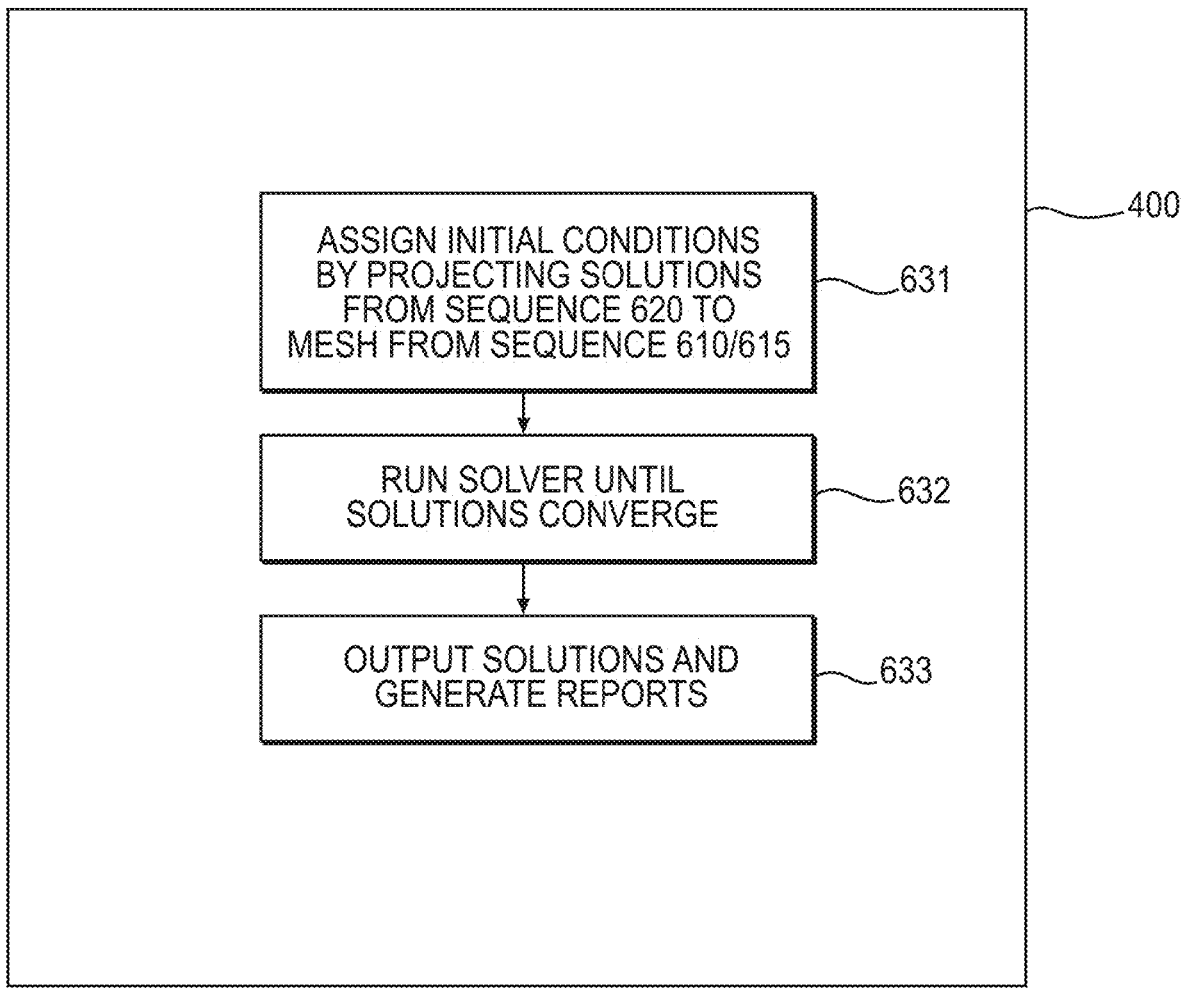
FIG. 9 is a flow chart of substeps of one of the steps of the method illustrated in FIGS. 4A-4C, according to an exemplary embodiment.

Referring now to FIG. 9, step 400 of performing computational analysis and outputting results may include several operations in some embodiments. For example, a first operation 631 may involve assigning initial conditions by projecting solutions from sequence 620 onto the mesh from sequence 610 or sequence 615. In other words, operation 613 may involve using linear interpolation to project the solution field computed in sequence 620 onto the refined mesh created in sequence 610 or sequence 615.

Next, a second operation 632 may use the projected solution field and the refined mesh created in 610 or 615 to solve the equations that govern the mathematical model to obtain a fully converged solution on the refined mesh. Finally, a third operation 633 may involve outputting solutions and generating reports, based on the solved mathematical equations. Such solutions may include, for example, any of a number of various blood flow characteristics or parameters, such as blood flow velocity, blood pressure (or a ratio thereof), flow rate, and FFR at various locations in the aorta, the main coronary arteries, and/or other coronary arteries or vessels downstream from the main coronary arteries. As mentioned previously, additional details regarding the step of performing computational analysis and outputting results are provided in U.S. patent application Ser. No. 13/013,561, which was previously incorporated by reference.

Any aspect set forth in any embodiment may be used with any other embodiment set forth herein. Every device and apparatus set forth herein may be used in any suitable medical procedure, may be advanced through any suitable body lumen and body cavity, and may be used for imaging any suitable body portion.

Various modifications and variations can be made in the disclosed systems and processes without departing from the scope of the disclosure. Other embodiments will be apparent to those skilled in the art from consideration of the specification and practice of the disclosure disclosed herein. It is intended that the specification and examples be considered as exemplary only, with a true scope and spirit of the disclosure being indicated by the following claims.

What is claimed is:

1. A system for noninvasively determining at least one physiological characteristic of a patient, the system comprising:
at least one computer system configured to, using a hardware processor of the at least one computer system:
receive a patient-specific surface model and physiological parameters;
identify, based on the received patient-specific surface model and physiological parameters, a high complexity portion of a surface mesh model as directing a flow of a blood volume having a first level of blood flow pattern complexity;
identify, based on the received patient-specific surface model and physiological parameters, a low complexity portion of the surface mesh model as directing a flow of a blood volume having a second level of blood flow pattern complexity that is less than the first level;
generate a surface mesh based on the identified high complexity portion and the identified low complexity portion of the surface mesh model;
generate, using a meshing library, a volume mesh based on the surface mesh;
obtain one or more solutions to one or more equations related to the at least one physiological characteristic of the patient based on the surface mesh and the volume mesh;
create a three-dimensional combined surface and volume mesh model based on the surface mesh, the volume mesh, and the one or more solutions, wherein the three-dimensional combined surface and volume mesh model includes at least a high resolution model portion corresponding to the high complexity portion and a low resolution model portion corresponding to the low complexity portion, the high resolution model portion having a spatial resolution that is greater than the low resolution model portion based upon one or more mesh points residing in or near a stenosed vessel portion of the three-dimensional combined surface and volume mesh model that is more complex than other portions of the combined surface and volume mesh model, wherein a size of a local mesh element associated with one of the one or more mesh points is based on a minimum cross-sectional area of the stenosed vessel of the combined surface and volume mesh model;

input the three-dimensional combined surface and volume mesh model into a fluid simulation system; and determine a measurement of the at least one physiological characteristic, using the fluid simulation system.

2. The system of claim 1, wherein the at least one computer system is further configured to estimate, using the combined surface and volume mesh model, a solution to at least one equation, before the inputting step, wherein the solution is input into the fluid simulation system along with the combined surface and volume mesh model.

3. The system of claim 1, wherein the at least one computer system is further configured to provide data for use by the fluid simulation system in determining the measurement, wherein the data is selected from the group consisting of surface and volume mesh coordinates, surface and volume element connectivities, model inlet and outlet coordinates and connectivities, and boundary and initial conditions.

4. The system of claim 1, wherein the at least one computer system is further configured to assign, before the obtaining the one or more solutions to the one or more equations, velocity value and pressure value to the surface mesh or the volume mesh.

5. The system of claim 1, wherein the obtaining the one or more solutions to the one or more equations comprises running a solver until the one or more solutions converge.

6. The system of claim 1, wherein the at least one computer system is further configured to prescribe a local mesh element size based on a minimum cross-sectional area of the stenosed vessel of the combined surface and volume mesh model.

7. The system of claim 1, wherein the at least one computer system is further configured to compute estimates of solution errors at each mesh point.

8. The system of claim 1, wherein the at least one computer system is further configured to:
read model geometry of the combined surface and volume mesh model and solution information computed by the computer system; and
generate estimates of solution errors for each of the mesh points.

9. The system of claim 8, wherein the at least one computer system is further configured to:
based on the solution errors, determining a desired mesh size for the combined surface and volume mesh model at each of the mesh points, wherein the desired mesh size is configured to achieve a solution error that is approximately uniform at approximately all mesh points; and
based on the desired mesh sizes, identifying the mesh points that will be refined.

10. A method for noninvasively determining at least one physiological characteristic of a patient using a computer system, the method comprising:
receiving a patient-specific surface model and physiological parameters;
identifying, based on the received patient-specific surface model and physiological parameters, a high-complexity portion of a surface mesh model as directing a flow of a blood volume having a first level of blood flow pattern complexity;
identifying, based on the received patient-specific surface model and physiological parameters, a low complexity portion of the surface mesh model as directing a flow of a blood volume having a second level of blood flow pattern complexity that is less than the first level;
generating a surface mesh based on the identified high complexity portion and the identified low complexity portion of the surface mesh model;
generating, using a meshing library, a volume mesh based on the surface mesh;
obtaining one or more solutions to one or more equations related to the at least one physiological characteristic of the patient based on the surface mesh and the volume mesh;
creating a three-dimensional combined surface and volume mesh model based on the surface mesh, the volume mesh, and the one or more solutions, wherein the three-dimensional combined surface and volume mesh model includes at least a high resolution model portion corresponding to the high complexity portion and a low resolution model portion corresponding to the low complexity portion, the high resolution model portion having a spatial resolution that is greater than the low resolution model portion based upon one or more mesh points residing in or near a stenosed vessel portion of the three-dimensional combined surface and volume mesh model that is more complex than other portions of the combined surface and volume mesh model, wherein a size of a local mesh element associated with one of the one or more mesh points is based on a minimum cross-sectional area of the stenosed vessel of the combined surface and volume mesh model;
processing the combined surface and volume mesh model to generate a refined surface and volume mesh model;
inputting the refined surface and volume mesh model into a fluid simulation system of the computer system; and
determining a measurement of the at least one physiological characteristic, using the fluid simulation system and based on the refined surface and volume mesh model.

11. The method of claim 10, further comprising processing the surface mesh model before the identifying steps to generate a refined surface mesh model, wherein the identifying steps are performed on the refined surface mesh model.

12. The method of claim 10, further comprising, after creating the combined surface and volume mesh model:
generating at least one solution to at least one equation based on the combined surface and volume mesh model; and
using linear interpolation to project the at least one solution onto the combined surface and volume mesh model.

13. The method of claim 10, further comprising, identifying the one or more mesh points by detecting mesh points within a predetermined distance from a centerline point located in an ostium of the combined surface and volume mesh model.

14. The method of claim 10, further comprising, before the inputting step, generating at least one solution to at least one equation, based on the combined surface and volume mesh model, wherein the inputting step further comprises inputting the at least one solution into the fluid simulation system along with the combined surface and volume mesh model.

15. A non-transitory computer readable medium for use on at least one computer system containing computer-executable programming instructions for performing a method for noninvasively determining at least one physiological characteristic of a patient, the method comprising:

receiving a patient-specific surface model and physiological parameters;

identifying, based on the received patient-specific surface model and physiological parameters, a high-complexity portion of a three-dimensional surface mesh model as directing a flow of a blood volume having a first level of blood flow pattern complexity;

identifying, based on the received patient-specific surface model and physiological parameters, a low complexity portion of the surface mesh model as directing a flow of a blood volume having a second level of blood flow pattern complexity that is less than the first level;

generating a surface mesh based on the identified high complexity portion and the identified low complexity portion of the surface mesh model;

generating, using a meshing library, a volume mesh based on the surface mesh;

obtaining one or more solutions to one or more equations related to the at least one physiological characteristic of the patient based on the surface mesh and the volume mesh;

creating a three-dimensional combined surface and volume mesh model based on the surface mesh, the volume mesh, and the one or more solutions, wherein the three-dimensional combined surface and volume mesh model includes at least a high resolution model portion corresponding to the high complexity portion and a low resolution model portion corresponding to the low complexity portion, the high resolution model portion having a spatial resolution that is greater than the low resolution model portion based upon one or more mesh points residing in or near a stenosed vessel portion of the three-dimensional combined surface and volume mesh model that is more complex than other portions of the combined surface and volume mesh model, wherein a size of a local mesh element associated with one of the one or more mesh points is based on a minimum cross-sectional area of the stenosed vessel of the combined surface and volume mesh model;

generating at least one solution to at least one equation, based on the combined surface and volume mesh model;

inputting the combined surface and volume mesh model and the at least one solution into a fluid simulation system of the computer system; and determining a measurement of the at least one physiological characteristic, using the fluid simulation system and based on the combined surface and volume mesh model and the at least one solution.

16. The non-transitory computer readable medium of claim 15, wherein each of the one or more mesh points is within a predetermined distance from a centerline point located in the ostium of the combined surface and volume mesh model.

17. The non-transitory computer readable medium of claim 15, wherein the method further comprises:

reading a model geometry of the combined surface and volume mesh model and solution information computed by the computer system; and generating estimates of solution errors for each of the mesh points.

18. The non-transitory computer readable medium of claim 17, wherein the method further comprises:

based on the solution errors, determining a desired mesh size for the combined surface and volume mesh model at each of the mesh points, wherein the desired mesh size is configured to achieve a solution error that is approximately uniform at approximately all mesh points; and based on the desired mesh sizes, identifying the mesh points that will be refined.

19. The non-transitory computer readable medium of claim 15, wherein the method further comprises prescribing a local mesh element size based on a minimum cross-sectional area of the stenosed vessel.

* * * * *